United States Patent
Mori et al.

(10) Patent No.: US 10,835,466 B2
(45) Date of Patent: Nov. 17, 2020

(54) WRINKLE AMELIORATING AGENT

(71) Applicant: POLA CHEMICAL INDUSTRIES, INC., Fukuroi (JP)

(72) Inventors: Yasuhito Mori, Yokohama (JP); Yuko Saitoh, Yokohama (JP); Michiko Shono, Yokohama (JP)

(73) Assignee: POLA CHEMICAL INDUSTRIES, INC., Shizuoka (JP)

( * ) Notice: Subject to any disclaimer, the term of this patent is extended or adjusted under 35 U.S.C. 154(b) by 0 days.

(21) Appl. No.: 16/464,250

(22) PCT Filed: Nov. 27, 2017

(86) PCT No.: PCT/JP2017/042338
§ 371 (c)(1),
(2) Date: May 24, 2019

(87) PCT Pub. No.: WO2018/097274
PCT Pub. Date: May 31, 2018

(65) Prior Publication Data
US 2019/0388317 A1  Dec. 26, 2019

(30) Foreign Application Priority Data

Nov. 28, 2016  (JP) .................................. 2016-230134

(51) Int. Cl.
*A61K 8/41* (2006.01)
*A61Q 19/08* (2006.01)

(52) U.S. Cl.
CPC ................ *A61K 8/41* (2013.01); *A61Q 19/08* (2013.01)

(58) Field of Classification Search
CPC .................................. A61K 8/41; A61Q 19/08
See application file for complete search history.

(56) References Cited

U.S. PATENT DOCUMENTS

| | | | |
|---|---|---|---|
| 5,578,324 A | 11/1996 | Dohi et al. | |
| 5,719,197 A * | 2/1998 | Kanios | A61F 13/0276 |
| | | | 424/435 |
| 2009/0098207 A1 * | 4/2009 | Malakhov | A61K 9/5089 |
| | | | 424/489 |
| 2010/0016442 A1 | 1/2010 | Cohen et al. | |
| 2010/0292509 A1 | 11/2010 | Kajiya et al. | |

FOREIGN PATENT DOCUMENTS

| | | | |
|---|---|---|---|
| JP | 58046049 | * | 3/1983 |
| JP | S58-46049 A | | 3/1983 |
| JP | S63-270650 A | | 11/1988 |
| JP | S644508 B2 | | 1/1989 |
| JP | H03-83912 A | | 4/1991 |
| WO | 9503818 A1 | | 2/1995 |
| WO | 2009093534 A1 | | 7/2009 |

OTHER PUBLICATIONS

International Search Report in PCT/JP2017/042338, dated Feb. 13, 2018, pp. 1-4.

* cited by examiner

*Primary Examiner* — Shirley V Gembeh
(74) *Attorney, Agent, or Firm* — Knobbe, Martens, Olson & Bear, LLP

(57) ABSTRACT

The object is to provide a wrinkle improving agent having an excellent wrinkle improving effect. A compound expressed by the following Formula (1), or an acid addition salt thereof is used as an active ingredient of a wrinkle improving agent.

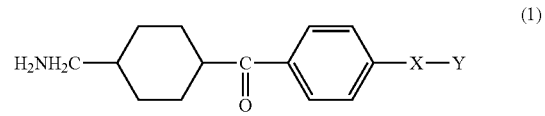

(1)

(Wherein X represents an alkylene group having 1 to 2 carbon atoms in which a hydrogen atom may be substituted with a methyl group, Y represents $COOR^1$ or $CH_2OR^2$, $R^1$ represents a hydrogen atom, or an optionally branched alkyl group having 1 to 6 carbon atoms, and $R^2$ represents a hydrogen atom, or an optionally branched acyl group having 1 to 6 carbon atoms.)

3 Claims, No Drawings

WRINKLE AMELIORATING AGENT

TECHNICAL FIELD

The present invention relates to a wrinkle improving agent having an excellent wrinkle improving effect.

BACKGROUND ART

The wrinkle is one of skin aging symptoms caused by aging, stress, exposure to ultraviolet rays, or the like, which greatly affects the impression of a face because it is easily recognizable. Therefore, interest in wrinkle and its improvement method is very high.

Conventionally, a moisturizing means using an external preparation for skin containing a polymer having a water retention capacity such as mucopolysaccharide or collagen has been adopted to improve wrinkles. However, it alone could not improve wrinkles sufficiently.

Meanwhile, the mechanism of wrinkle formation is complicated, and it is difficult to replicate it experimentally, so the mechanism has not been fully elucidated even now. Nonetheless, in recent studies, it has become clear that not only aging is an important factor, but also drying, oxidation, glycosylation, ultraviolet rays, etc. are factors that affect greatly skin aging symptoms. Specifically, the factors, especially exposure to ultraviolet rays, cause cell damage and thereby enhanced apoptosis of cells, decrease in the turnover rate of a fibrillary element such as collagen due to decline in the proliferation activity of fibroblasts, which are the principal cells in the dermis, or in the synthesis function of collagen, etc., collapse of a fiber bundle due to increase in inflammatory cytokine, accumulation of waste matter due to reduction of the vascular system, decrease in nutrient supply, and the like. As a result, the elasticity of the skin is conceivably lost to generate wrinkles.

Since there are many factors which have influences on the mechanism of generation of wrinkles in complicated manners as described above, various ingredients have been proposed for a wrinkle improving agent. For example, it is known that retinol and its metabolite retinoic acid, an amino acid, such as alanine and glycine, a macromolecule, such as collagen and hyaluronic acid, ascorbic acid, tocopherol, and the like have a wrinkle improving effect. Further, it has been reported that a tranexamic acid amide derivative can also promote production of vascular endothelial growth factor C, and can become an active ingredient of a wrinkle improving agent (Patent Literature 1).

However, the wrinkle improvement effect of the conventional wrinkle improving agent was not fully satisfactory, or brought about in some cases undesirable other effects (side reactions) at a concentration effective in exerting the wrinkle improving effect. Therefore, there is a demand for a new ingredient that exerts a wrinkle improving effect.

In this regard, it has been confirmed that the aminocarboxylic acid derivative described in Patent Literature 2 has an antiulcer action, and its use as a pharmaceutical product has been proposed. Incidentally, the structure of the compound partially agrees with that of tranexamic acid.

CITATION LIST

Patent Literature

[Patent Literature 1] International Publication No. WO 2009/093534

[Patent Literature 2] Japanese Examined Patent Publication No. 64-4508

SUMMARY OF INVENTION

Technical Problem

An object of the present invention is to provide a wrinkle improving agent having an excellent wrinkle improving effect.

Solution to Problem

The present inventors conducted intensive studies in search of a compound having a wrinkle improving effect to find that an aminocarboxylic acid derivative having a specific structure and an acid addition salt thereof exert an excellent anti-wrinkle effect, thereby completing the present invention.

That is, an aspect of the present invention is a wrinkle improving agent comprising a compound expressed by the following Formula (1), or an acid addition salt thereof.

[Chem. 1]

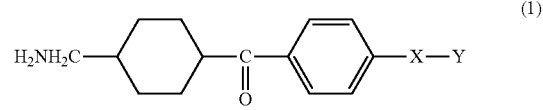

(Wherein X represents an alkylene group having 1 to 2 carbon atoms in which a hydrogen atom may be substituted with a methyl group, Y represents $COOR^1$ or $CH_2OR^2$, $R^1$ represents a hydrogen atom, or an optionally branched alkyl group having 1 to 6 carbon atoms, and $R^2$ represents a hydrogen atom, or an optionally branched acyl group having 1 to 6 carbon atoms.)

Another aspect of the present invention is an external composition for skin for wrinkle improvement containing the wrinkle improving agent. The external composition for skin is preferably a cosmetic.

Advantageous Effects of Invention

According to the present invention, a wrinkle improving agent having an excellent wrinkle improving effect is provided. In addition, an external composition for skin for wrinkle improvement containing the wrinkle improving agent is also provided, which is suitable as cosmetic. Such an external composition for skin is in line with the trend of the times expecting an anti-aging effect from a cosmetic, and it meets the needs of consumers.

DETAILED DESCRIPTION OF THE PREFERRED EMBODIMENT

The wrinkle improving agent of the present invention contains a compound expressed by the following Formula (1) or an acid addition salt thereof.

[Chem. 2]

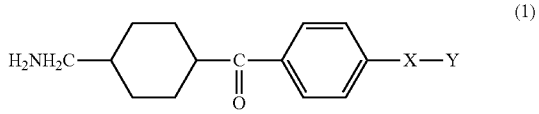

In Formula (1), X represents an alkylene group having 1 to 2 carbon atoms, in which a hydrogen atom may be substituted with a methyl group. The alkylene group having 1 to 2 carbon atoms is a methylene group, and an ethylene group. X is preferably —CH(CH$_3$)—, or —CH$_2$—CH$_2$—.

In Formula (I), Y represents COOR$^1$ or CH$_2$OR$^2$, R$^1$ represents a hydrogen atom, or an optionally branched alkyl group having 1 to 6 carbon atoms, and R$^2$ represents a hydrogen atom, or an optionally branched acyl group having 1 to 6 carbon atoms.

That is, in a case where Y is COOR$^1$, when R$^1$ is a hydrogen atom, Y is a carboxyl group; and when R$^1$ is an optionally branched alkyl group having 1 to 6 carbon atoms, Y is an ester group. Examples of the optionally branched alkyl group having 1 to 6 carbon atoms include a methyl group, an ethyl group, a n-propyl group, an isopropyl group, a n-butyl group, an isobutyl group, a tert-butyl group, a n-pentyl group, and a n-hexyl group. From the viewpoint of wrinkle improving effect, R$^1$ is particularly preferably a hydrogen atom, and when R$^1$ is an alkyl group, it is more preferable that the carbon number thereof is small.

Also, in a case where Y is CH$_2$OR$^2$, when R$^1$ is a hydrogen atom, Y is a hydroxymethyl group; and when R$^2$ is an optionally branched acyl group having 1 to 6 carbon atoms, Y is an ester group. Examples of the optionally branched acyl group having 1 to 6 carbon atoms include a formyl group, an acetyl group, an acryloyl group, a propionyl group, a propioloyl group, a butyryl group, an isobutyryl group, a methacryloyl group, a valeryl group, and a caproyl group. From the viewpoint of wrinkle improving effect, R$^2$ is particularly preferably a hydrogen atom, and when R$^2$ is an acyl group, it is more preferable that the carbon number thereof is small.

In Formula (1), the conformation of the 1,4-cyclohexylene group may be either of the chair shape and the boat shape. Also, the two free bonds may be in either cis or trans relationship. Preferably, they are in the trans relationship with a chair shape conformation.

Examples of an acid addition salt of the compound expressed by the following Formula (1) include salts with an inorganic acid, an organic carboxylic acid, or an organic sulfonic acid. Examples of the inorganic acid include hydrochloric acid, hydrobromic acid, sulfuric acid, nitric acid, and phosphoric acid. Examples of the organic carboxylic acid include acetic acid, propionic acid, maleic acid, fumaric acid, oxalic acid, citric acid, butyric acid, lactic acid, and tartaric acid. Examples of the organic sulfonic acid include methanesulfonic acid, ethanesulfonic acid, benzenesulfonic acid, and p-toluenesulfonic acid. Among them, the inorganic acid salt is preferable, and a hydrochloride salt is more preferable.

As an active ingredient of the wrinkle improving agent of the present invention, any of compounds expressed by Formula (1) or acid addition salts thereof may be used, however, the acid addition salts are more preferable.

Specific examples of the compound expressed by Formula (1) are listed below, but needless to say, the compound is not limited thereto. 2-[p-(4-aminonethylcyclohexylcarbonyl)phenyl]acetic acid, methyl 2-[p-(4-aminomethylcyclohexylcarbonyl)phenyl]acetate, ethyl 2-[p-(4-aminomethylcyclohexylcarbonyl)phenyl]acetate, propyl 2-[p-(4-aminomethylcyclohexylcarbonyl)phenyl]acetate, butyl 2-[p-(4-aminomethylcyclohexylcarbonyl)phenyl]acetate, pentyl 2-[p-(4-aminomethyl cyclohexylcarbonyl)phenyl]acetate, hexyl 2-[p-(4-aminomethylcyclohexylcarbonyl)phenyl]acetate; 2-[p-(4-aminomethylcyclohexylcarbonyl)phenyl]ethanol. 2-[p-(4-aminomethylcyclohexylcarbonyl)phenyl]ethyl formate, 2-[p-(4-aminomethyl cyclohexylcarbonyl)phenyl]ethyl acetate, 2-[p-(4-aminomethylcyclohexylcarbonyl)phenyl]ethyl propionate, 2-[p-(4-aminomethylcyclohexylcarbonyl)phenyl]ethyl butyrate, 2-[p-(4-aminomethylcyclohexylcarbonyl)phenyl]ethyl pentanoate, 2-[p-(4-aminomethylcyclohexylcarbonyl)phenyl] ethyl hexanoate; 2-[p-(4-aminomethylcyclohexylcarbonyl)phenyl]propionic acid, methyl 2-[p-(4-aminomethylcyclohexylcarbonyl)phenyl]propionate, ethyl 2-[p-(4-aminomethylcyclohexylcarbonyl)phenyl]propionate, propyl 2-[p-(4-aminomethylcyclohexylcarbonyl)phenyl]propionate, butyl 2-[p-(4-aminomethylcyclohexylcarbonyl)phenyl]propionate, pentyl 2-[p-(4-aminomethyl cyclohexylcarbonyl)phenyl]propionate, hexyl 2-[p-(4-aminomethylcyclohexylcarbonyl)phenyl]propionate; 2-[p-(4-aminomethylcyclohexylcarbonyl)phenyl]propanol, 2-[p-(4-aminomethylcyclohexylcarbonyl)phenyl]propyl formate, 2-[p-(4-aminomethyl cyclohexylcarbonyl)phenyl]propyl acetate, 2-[p-(4-aminomethylcyclohexylcarbonyl)phenyl] propyl propionate, 2-[p-(4-aminomethylcyclohexylcarbonyl)phenyl]propyl butyrate, 2-[p-(4-aminomethylcyclohexylcarbonyl)phenyl]propyl pentanoate, 2-[p-(4-aminomethylcyclohexylcarbonyl)phenyl]propyl hexanoate; 3-[p-(4-aminomethylcyclohexylcarbonyl)phenyl]propionic acid (compound 1), ethyl 3-[p-(4-aminomethylcyclohexylcarbonyl)phenyl]propionate, propyl 3-[p-(4-aminomethylcyclohexylcarbonyl)phenyl]propionate, butyl 3-[p-(4-aminomethylcyclohexylcarbonyl)phenyl]propionate, pentyl 3-[p-(4-aminomethylcyclohexylcarbonyl)phenyl]propionate, hexyl 3-[p-(4-aminomethylcyclohexylcarbonyl)phenyl]propionate (compound 2); 3-[p-(4-aminomethylcyclohexylcarbonyl)phenyl]propanol (compound 3), 3-[p-(4-aminomethylcyclohexylcarbonyl)phenyl]propyl formate, 3-[p-(4-aminomethylcyclohexylcarbonyl)phenyl]propyl acetate, 3-[p-(4-aminomethylcyclohexylcarbonyl)phenyl]propyl propionate, 3-[p-(4-aminomethylcyclohexylcarbonyl)phenyl]propyl butyrate, 3-[p-(4-aminomethylcyclohexylcarbonyl)phenyl]propyl pentanoate, 3-[p-(4-aminomethylcyclohexylcarbonyl)phenyl]propyl hexanoate (compound 4), 2-methyl-3-[p-(4-aminomethylcyclohexylcarbonyl)phenyl]propanol, 2-methyl-3-[p-(4-aminomethylcyclohexylcarbonyl)phenyl]propyl formate. 2-methyl-3-[p-(4-aminomethylcyclohexylcarbonyl)phenyl]propyl acetate. 2-methyl-3-[p-(4-aminomethylcyclohexylcarbonyl)phenyl]propyl propionate, 2-methyl-3-[p-(4-aminomethylcyclohexylcarbonyl)phenyl]propyl butyrate, 2-methyl-3-[p-(4-aminomethylcyclohexylcarbonyl)phenyl]propyl pentanoate, and 2-methyl-3-[p-(4-aminomethylcyclohexylcarbonyl)phenyl]propyl hexanoate (compound 5).

[Chem. 3]

(Compound 1)

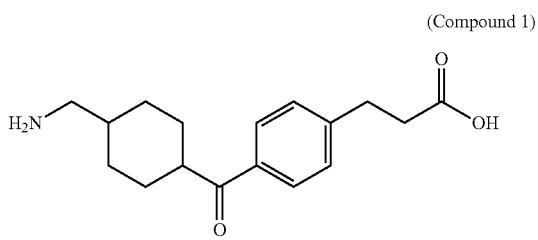

[Chem. 4]

(Compound 2)

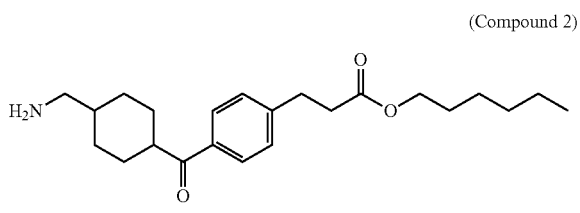

[Chem. 5]

(Compound 3)

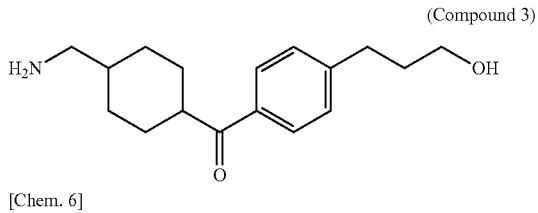

[Chem. 6]

(Compound 4)

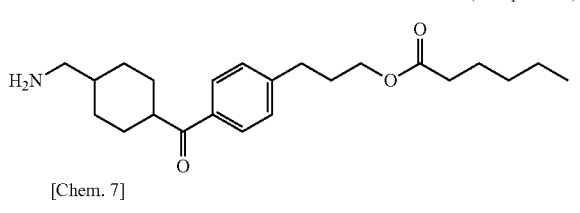

[Chem. 7]

(Compound 5)

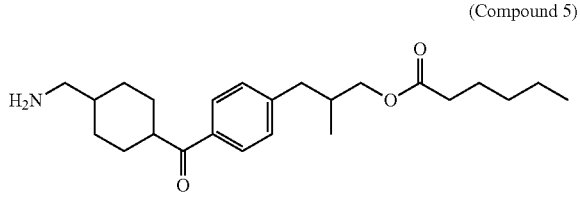

The compound expressed by Formula (1) can be obtained through synthesis and purification according to conventional methods. For example, it can be synthesized by an acylation reaction in the presence of a Lewis acid of an acid addition salt of an aminocarboxylic acid halide described in Patent Literature 2, and then through a suitable isolation and purification method.

Since the compound expressed by Formula (1) or an acid addition salt thereof has an excellent wrinkle improving effect, the same constitutes an active ingredient of a wrinkle improving agent.

The term "wrinkle improvement" means herein that skin grooves become shallow or thin, and wrinkles become less conspicuous.

From another viewpoint, the present invention may be understood as a method for wrinkle-improving comprising application of a compound expressed by Formula (1) or an acid addition salt thereof.

From another viewpoint, the present invention may be understood as a use of a compound expressed by Formula (1) or an acid addition salt thereof for wrinkle improvement.

From another viewpoint, the present invention may be understood as a use of a compound expressed by Formula (1) or an acid addition salt thereof for producing a wrinkle improving agent.

From another viewpoint, the present invention may be understood as a compound expressed by Formula (1) or an acid addition salt thereof used for improving the wrinkle.

The structure of a compound expressed by Formula (1) partially agrees with that of tranexamic acid or the tranexamic acid amide derivative described in Patent Literature 1, however it has been known that that the compound is not metabolized to tranexamic acid in vivo. That is, the wrinkle improving effect of the compound expressed by Formula (1) is thought to be due to a mechanism different from that with the tranexamic acid amide derivative. It is presumed that at least the structure of the (4-aminomethyl-cyclohexylcarbonyl)phenyl group participates in development of the effect.

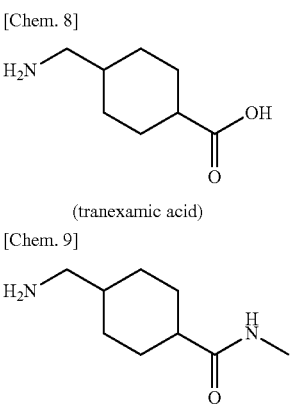

A wrinkle improving agent of the present invention may be contained in a wrinkle improving composition, and particularly preferably in an external composition for skin, from which an effect can be expected by percutaneous absorption. There is no particular restriction on the form of the external composition for skin, insofar as it can be applied to the skin externally, and preferable examples thereof include a cosmetic (including a quasi-drug), and medicinal products. Since high safety has been confirmed with respect to the compounds expressed by Formula (1), the same may be continuously applied in the form of a cosmetic which is routinely used.

There is no particular restriction on the formulation of the external composition for skin, and examples thereof include a lotion formulation, an emulsion formulation (O/W type, W/O type, etc.), such as milky lotion or cream, an oil formulation, a gel formulation, a pack, and a cleanser.

In a case where a wrinkle improving agent of the present invention is blended in a wrinkle improving external composition for skin, when the amount thereof with respect to the total amount of the composition is preferably from 0.01% to 20% by mass, and more preferably from 0.1 to 10% by mass, a desired effect can be easily obtained, and the design flexibility of the recipe can be secured.

An external composition for skin for wrinkle improvement according to the present invention may optionally contain ingredients to be incorporated commonly in an external composition for skin in addition to a wrinkle improving agent of the present invention to the extent that the advantageous effects of invention are not impaired.

Examples of such ingredients include an oil and wax, such as a macadamia nut oil, an avocado oil, a corn oil, an olive oil, a rapeseed oil, a sesame oil, a castor oil, a safflower oil, a cottonseed oil, a jojoba oil, a coconut oil, a palm oil, a liquid lanolin, a hydrogenated coconut oil, a hydrogenated oil, a Japan wax, a hydrogenated castor oil, a bees wax, a candelilla wax, a carnauba wax, an insect wax, lanolin, a reduced lanolin, a hard lanolin, and a jojoba wax; a hydrocarbon, such as liquid paraffin, squalane, pristane, ozokerite, paraffin, ceresin, petrolatum, and a microcrystalline wax; a higher fatty acid, such as oleic acid, isostearic acid, lauric acid, myristic acid, palmitic acid, stearic acid, behenic acid, and undecylenic acid; a higher alcohol, such as cetyl alcohol, stearyl alcohol, isostearyl alcohol, behenyl alcohol, octyldodecanol, myristyl alcohol, and cetostearyl alcohol; a synthetic ester oil, such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethylhexanoate, neopentyl glycol dicaprate, glycerol di-2-heptylundecanoate, glycerol tri-2-ethylhexanoate, trimethylolpropane tri-2-ethylhexanoate, trimethylolpropane triisostearate, and pentaerythit tetra-2-ethylhexanoate; an open-chain polysiloxane, such as dimethylpolysiloxane, methylphenylpolysiloxane, and diphenylpolysiloxane; a cyclic polysiloxane, such as octamethylcyclotetrasiloxane, decamethylcyclopentasiloxane, and dodecamethylcyclohexasiloxane; and an oil like a silicone oil as a modified polysiloxane, such as an amino-modified polysiloxane, a polyether-modified polysiloxane, an alkyl-modified polysiloxane, and a fluorine-modified polysiloxane;

An anionic surfactant, such as fatty acid soap (sodium laurate, sodium palmitate, etc.), potassium lauryl sulfate, and triethanolamine alkyl ether sulfate; a cationic surfactant, such as stearyl trimethyl ammonium chloride, benzalkonium chloride, and lauryl amine oxide; an amphoteric surfactant, such as an imidazoline type amphoteric surfactant (2-cocoyl-2-imidazolinium hydroxide-1-carboxyethyloxy disodium salt, etc.), a betaine type surfactant (alkylbetaine, amidobetaine, sulfobetaine, etc.), and acylmethyltaurine; a nonionic surfactant, such as a sorbitan fatty acid ester (sorbitan monostearate, sorbitan sesquioleate, etc.), a glycerol fatty acid (glycerol monostearate, etc.), a propylene glycol fatty acid ester (propylene glycol monostearate, etc.), a hydrogenated castor oil derivative, a glycerol alkyl ether, a POE sorbitan fatty acid ester (POE sorbitan monooleate, polyoxyethylene sorbitan monostearate, etc.), a POE sorbit fatty acid ester (POE-sorbit monolaurate, etc.), a POE glycerol fatty acid ester (POE glycerol monoisostearate, etc.), a POE fatty acid ester (poly(ethylene glycol) monooleate, POE distearate, etc.), a POE alkyl ether (POE 2-octyldodecyl ether, etc.), a POE alkylphenyl ether (POE nonylphenyl ether, etc.), Pluronic series, a POE-POP alkyl ether (POE-POP 2-decyltetradecyl ether, etc.), Tetronic series, a POE castor oil or hydrogenated castor oil derivative (POE castor oil, POE hydrogenated castor oil, etc.), a sucrose fatty acid ester, and an alkyl glucoside; a polyhydric alcohol, such as poly(ethylene glycol), glycerol, 1,3-butylene glycol, erythritol, sorbitol, xylitol, maltitol, propylene glycol, dipropylene glycol, diglycerol, isoprene glycol, 1,2-pentanediol, 2,4-hexanediol, 1,2-hexanediol, and 1,2-octanediol;

A moisturizing component, such as sodium pyrrolidone carboxylate, lactic acid, and sodium lactate; a powder, which may be optionally surface-treated, such as mica, talc, kaolin, synthetic mica, calcium carbonate, magnesium carbonate, anhydrous silicic acid (silica), aluminum oxide, and barium sulfate; an inorganic pigment, which may be optionally surface-treated, such as Bengal red, yellow iron oxide, black iron oxide, cobalt oxide, ultramarine blue, iron blue, titanium oxide, and zinc oxide; a pearling agent, which may be optionally surface-treated, such as titanated mica, fish scale flake, and bismuth oxychloride; an organic dye, which may be optionally laked, such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Violet No. 201, and Red No. 204; an organic powder, such as a polyethylene powder, poly(methyl methacrylate), a nylon powder, and an organopolysiloxane elastomer; a p-aminobenzoic acid type ultraviolet absorber; an anthranilic acid type ultraviolet absorber; a salicylic acid type ultraviolet absorber; a cinnamic acid type ultraviolet absorber; a benzophenone type ultraviolet absorber; a sugar type ultraviolet absorber; an ultraviolet absorber, such as 2-(2'-hydroxy-5'-t-octylphenyl)benzotriazole, and 4-methoxy-4'-t-butyldibenzoylmethane;

A lower alcohol, such as ethanol, and isopropanol; a vitamin B, such as vitamin A or its derivatives, vitamin B or its derivatives, vitamin $B_6$ hydrochloride, vitamin $B_6$ tripalmitate, vitamin $B_6$ dioctanoate, vitamin $B_2$ or its derivatives, vitamin $B_{12}$, and vitamin $B_{15}$ or its derivatives; a vitamin, a vitamin E, such as α-tocopherol, β-tocopherol, γ-tocopherol, and vitamin E acetate; other vitamins, such as a vitamin D, vitamin H, pantothenic acid, pantethine, and pyrroloquinoline quinone; an antimicrobial agent (preservative), such as methylparaben, ethylparaben, butylparaben, and phenoxyethanol; an anti-inflammatory agent, such as a glycyrrhizic acid derivative, a glycyrrhetinic acid derivative, a salicylic acid derivative, hinokitiol, zinc oxide, and allantoin; a whitening agent, such as an alkylresorcinol, a placenta extract, a saxifrage extract, and arbutin; various extracts (e.g., Phellodendron bark, Coptis Rhizome, Lithospermi radix, peony root, swertia herb, birch, sage, loquat, carrot, aloe, mallow, iris, grape, coix seed, loofah, lily, saffron, cnidium rhizome, ginger, *Hypericum*, Ononis, garlic, *Capsicum, Citrus* Unshiu peel, Japanese *Angelica* root, and seaweed, etc.; an activator, such as royal jelly, a photosensitizer, and a cholesterol derivative; a blood circulation promoter, such as nonylic acid vanillylamide, capsaicin, zingelon, and tannic acid; an antiseborrheic agent, such as sulfur, and thianthol; an anti-inflammatory agent, such as tranexamic acid, thiotaurine, and hypotaurine; and a water-soluble polymer, such as collagen and hyaluronic acid.

Further, a wrinkle improving agent other than the wrinkle improving agent of the present invention may be blended together in the external composition.

EXAMPLES

The present invention will be described in more detail below with reference to concrete experimental examples, provided that the present invention is not limited to the following aspects.

<Test of Wrinkle Improvement Effect>

The cosmetics (Examples 1-7, Comparative Example, and Reference Examples) according to Table 1 were prepared respectively in a conventional manner.

With regard to each of the prepared cosmetics, the wrinkle improvement effect was evaluated by the following method. In other words, 45 women (40 to 60 years old) who were concerned about wrinkles of the outer corners of the eyes were divided into 9 groups of 5 persons. To each group, any one of the cosmetics of Examples 1 to 7, Comparative Example, and Reference Examples was handed over, which was applied by them to the outer corners of the eyes twice a day in the morning and evening continuously for 8 weeks. Before and after the test, an impression of the skin surface profile was taken in a conventional manner to produce the respective replicas. As the base material for the replica, that for a white replica not transmitting light was used. The prepared replica was fixed on a sample stand of a stereomicroscope, and irradiated with light at an angle of 45 degrees, while the replica was rotated, so that a shadow image (1×1 cm$^2$) in the direction in which the shadow of a skin groove was observed with a high contrast was captured with an image analysis apparatus. In the image, according to an undulation of wrinkles, an area where a wrinkle is deep, exhibits a low brightness, and an area free from a wrinkle exhibits a high brightness, so as to form a shadowgram. The distribution of brightness in the shadow image was determined, and the brightness equal to or higher than the median value of the brightness was transformed to the maximum brightness, and the brightness below the median value was transformed to the brightness 0 so that binarization is performed according to the borderline of the median value of the brightness. Then the area rate of the shadow portion (portion with the brightness 0) was measured and the wrinkle improvement rate was calculated based on the following expression. The average value of each group is shown in Table 2.

Wrinkle improvement rate (%)=(Area rate of shadow portion before test−Area rate of shadow portion after test)/(Area rate of shadow portion before test)×100

TABLE 1

|  | (% by mass) |
| --- | --- |
| POE (60) hydrogenated castor oil | 0.1 |
| 1,3-Butanediol | 5 |
| Glycerol | 2 |
| Poly(ethylene glycol) 400 | 3 |
| 1,2-Pentanediol | 3 |
| Potassium hydroxide | 0.005 |
| Methylparaben | 0.2 |
| Compound in Table 2 | 1*[1] |
| Water | Balance |

*[1] 0.01 in Examples 3 and 5

TABLE 2

|  |  | Wrinkle improvement | |
| --- | --- | --- | --- |
|  | Compound | Improvement rate (%) | Evaluation*[2] |
| Example 1 | Hydrochloride salt of Compound 1 | 12.2 | AA |
| Example 2 | Compound 1 | 12 | AA |
| Example 3 | Compound 1 | 6.3 | A |
| Example 4 | Compound 3 | 9.3 | A |
| Example 5 | Compound 3 | 5.6 | A |
| Example 5 | Compound 2 | 8.2 | A |
| Example 6 | Compound 4 | 8.3 | A |
| Example 7 | Compound 5 | 6.5 | A |
| Comparative Example | None | 0.3 | B |
| Reference Example 1 | Tranexamic acid | 3.2 | B |
| Reference Example 2 | Tranexamic acid methylamide hydrochloride | 3.6 | B |

*[2] AA: The improvement rate is 10% or more, A: 5% or more and less than 10%, B: less than 5%

Production Example 1

A cosmetic lotion which was an external preparation for skin of the present invention was prepared according to the recipe shown in Table 3. That is, the ingredients of A were mixed at room temperature, and the ingredients of B were heated at 60° C. respectively and mixed together, then B was gradually added to A with stirring, and the mixture was cooled with stirring to yield a cosmetic lotion.

It was confirmed that this cosmetic lotion gave a wrinkle improvement effect when applied to the skin.

TABLE 3

|  | Cosmetic lotion | |
| --- | --- | --- |
|  |  | (% by mass) |
| A | Poly(ethylene glycol) | 0.5 |
|  | Glycerol | 10.0 |
|  | Pentylene glycol | 2.0 |
|  | Ethanol | 5.0 |
|  | Diglycerol | 1.0 |
|  | Citric acid | 0.1 |
|  | Sodium citrate | 0.1 |
|  | Methylparaben | 0.2 |
|  | Phenoxyethanol | 0.2 |
|  | Pentasodium pentetate | 0.1 |
|  | Xanthan gum | 0.1 |
|  | Hydrochloride salt of Compound 1 | 1.0 |
|  | Water | Balance |
| B | 1.3-Butylene glycol | 5.0 |
|  | PEG-60 Hydrogenated castor oil | 0.1 |
|  | Sucrose laurate | 0.2 |
|  | Perfume | 0.2 |
|  | Total | 100.0 |

Production Example 2

A cosmetic lotion which was an external preparation for skin of the present invention was prepared according to the recipe shown in Table 4. That is, the ingredients of A were mixed at room temperature, and the ingredients of B were heated at 60° C. respectively and mixed together, then B was gradually added to A with stirring, and the mixture was cooled with stirring to yield a cosmetic lotion.

It was confirmed that this cosmetic lotion gave a wrinkle improvement effect when applied to the skin.

TABLE 4

Cosmetic lotion

| | | (% by mass) |
|---|---|---|
| A | Poly(ethylene glycol) | 0.5 |
| | Glycerol | 10.0 |
| | Pentylene glycol | 2.0 |
| | Ethanol | 5.0 |
| | Diglycerol | 1.0 |
| | Citric acid | 0.1 |
| | Sodium citrate | 0.1 |
| | Methylparaben | 0.2 |
| | Phenoxyethanol | 0.2 |
| | Pentasodium pentetate | 0.1 |
| | Xanthan gum | 0.1 |
| | Hydrochloride salt of Compound 1 | 1.0 |
| | Water | Balance |
| B | 1,3-Butylene glycol | 5.0 |
| | PEG-60 Hydrogenated castor oil | 0.2 |
| | Sucrose laurate | 0.2 |
| | Glycerol tri(2-ethylhexanoate) | 1.0 |
| | Perfume | 0.2 |
| | Total | 100.0 |

Production Example 3

An essence which was an external preparation for skin of the present invention was prepared according to the recipe shown in Table 5. That is, the ingredients of A and B were heated at 80° C., and mixed together respectively, then B was gradually added to A with stirring, and the mixture was cooled with stirring to yield an essence.

It was confirmed that this essence gave a wrinkle improvement effect when applied to the skin.

TABLE 5

Essence

| | | (% by mass) |
|---|---|---|
| A | Poly(ethylene glycol) | 0.5 |
| | Glycerol | 10.0 |
| | Pentylene glycol | 2.0 |
| | Ethanol | 5.0 |
| | Diglycerol | 1.0 |
| | Citric acid | 0.1 |
| | Sodium citrate | 0.1 |
| | Potassium hydroxide | 0.1 |
| | Methylparaben | 0.2 |
| | Phenoxyethanol | 0.2 |
| | Pentasodium pentetate | 0.1 |
| | Arbutin | 3.0 |
| | Carbomer | 0.2 |
| | Xanthan gum | 0.1 |
| | Hydrochloride salt of Compound 1 | 1.0 |
| | Dipotassium glycyrrhizinate | 0.1 |
| | Water | Balance |
| B | 1,3-Butylene glycol | 5.0 |
| | PEG-60 Hydrogenated castor oil | 0.1 |
| | Sucrose laurate | 0.2 |
| | Perfume | 0.2 |
| | Total | 100.0 |

Production Example 4

A milky lotion which was an external preparation for skin of the present invention was prepared according to the recipe shown in Table 6. That is, the ingredients of A and B were heated at 80° C., and mixed together respectively, then B was gradually added to A with stirring, and the mixture was cooled with stirring to yield a milky lotion.

It was confirmed that this milky lotion gave a wrinkle improvement effect when applied to the skin.

TABLE 6

Milky lotion

| | | (% by mass) |
|---|---|---|
| A | Poly(ethylene glycol) | 0.5 |
| | 1,3-Butylene glycol | 5.0 |
| | Glycerol | 10.0 |
| | Pentylene glycol | 2.0 |
| | Ethanol | 5.0 |
| | Diglycerol | 1.0 |
| | Citric acid | 0.1 |
| | Sodium citrate | 0.1 |
| | Potassium hydroxide | 0.05 |
| | Calcium chloride | 0.02 |
| | Methylparaben | 0.2 |
| | Phenoxyethanol | 0.2 |
| | Pentasodium pentetate | 0.1 |
| | Arbutin | 3.0 |
| | Xanthan gum | 0.05 |
| | Acrylate/(C10-30) alkyl acrylate) crosspolymer | 0.2 |
| | Propylene glycol alginate | 0.5 |
| | Fermented liquor of royal jelly | 0.5 |
| | Hydrochloride salt of Compound 1 | 1.0 |
| | Dipotassium glycyrrhizinate | 0.1 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 1.0 |
| | Beeswax | 0.5 |
| | Dimethicone | 0.5 |
| | Methylphenylpolysiloxane | 0.5 |
| | Sorbitan stearate | 0.1 |
| | POE (20) sorbitan stearate | 0.1 |
| | PEG-25 stearate | 0.1 |
| | Sucrose stearate | 0.1 |
| | Stearic acid | 0.1 |
| | Cetanol | 0.5 |
| | Perfume | 0.2 |
| | Total | 100.0 |

Production Example 5

An O/W cream which was an external preparation for skin of the present invention was prepared according to the recipe shown in Table 7. That is, the ingredients of A and B were heated at 80° C., and mixed together respectively, then B was gradually added to A with stirring, and the mixture was cooled with stirring to yield an O/W cream.

It was confirmed that this O/W cream gave a wrinkle improvement effect when applied to the skin.

TABLE 7

O/W Cream

| | | (% by mass) |
|---|---|---|
| A | Poly(ethylene glycol) | 0.5 |
| | 1,3-Butylene glycol | 5.0 |
| | Glycerol | 10.0 |
| | Pentylene glycol | 2.0 |
| | Ethanol | 2.0 |
| | Diglycerol | 1.0 |
| | Citric acid | 0.1 |
| | Sodium citrate | 0.1 |
| | Potassium hydroxide | 0.4 |

TABLE 7-continued

| O/W Cream | | |
|---|---|---|
| | | (% by mass) |
| | Methylparaben | 0.2 |
| | Phenoxyethanol | 0.2 |
| | Pentasodium pentetate | 0.1 |
| | Ascorbic acid glucoside | 2.0 |
| | Xanthan gum | 0.05 |
| | Acrylate/(C10-30) alkyl acrylate) crosspolymer | 0.2 |
| | Hydrochloride salt of Compound 1 | 1.0 |
| | Dipotassium glycyrrhizinate | 0.1 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 1.0 |
| | Beeswax | 0.5 |
| | Dimethicone | 0.5 |
| | Methylphenyl polysiloxane | 0.5 |
| | Sorbitan stearate | 0.5 |
| | POE-20 sorbitan stearate | 0.5 |
| | PEG-25 stearate | 0.5 |
| | Sucrose stearate | 0.5 |
| | Stearic acid | 0.5 |
| | Cetanol | 1.0 |
| | Behenyl alcohol | 0.5 |
| | Ethylhexylglycerin | 0.2 |
| | Tocopherol | 0.1 |
| | Perfume | 0.2 |
| | Total | 100.0 |

Production Example 6

A W/O cream which was an external preparation for skin of the present invention was prepared according to the recipe shown in Table 8. That is, the ingredients of A and B were heated at 80° C., and mixed together respectively, then A was gradually added to B with stirring, and the mixture was cooled with stirring to yield a W/O cream.

It was confirmed that this W/O cream gave a wrinkle improvement effect when applied to the skin.

TABLE 8

| W/O Cream | | |
|---|---|---|
| | | (% by mass) |
| A | Poly(ethylene glycol) | 0.5 |
| | 1,3-Butylene glycol | 5.0 |
| | Glycerol | 15.0 |
| | Pentylene glycol | 2.0 |
| | Ethanol | 2.0 |
| | Diglycerol | 1.0 |
| | Citric acid | 0.1 |
| | Sodium citrate | 0.1 |
| | Methylparaben | 0.2 |
| | Phenoxyethanol | 0.2 |
| | Pentasodium pentetate | 0.1 |
| | ascorbic acid glucoside | 2.0 |
| | Hydrochloride salt of Compound 1 | 1.0 |
| | Dipotassium glycyrrhizinate | 0.1 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 1.0 |
| | Beeswax | 0.5 |
| | Dimethicone | 0.5 |
| | Methylphenylpolysiloxane | 0.5 |
| | Decamethylcyclopentasiloxane | 27.2 |
| | Sucrose stearate | 0.5 |
| | PEG-10 Dimethicone | 4.0 |
| | Dimethyl distearyl ammonium hectorite | 2.0 |
| | Ethylhexylglycerin | 0.2 |
| | Tocopherol | 0.1 |
| | Perfume | 0.2 |
| | Total | 100.0 |

Production Example 7

An O/W foundation which was an external preparation for skin of the present invention was prepared according to the recipe shown in Table 9. That is, the ingredients of A and B were heated at 80° C., and mixed together respectively, then B was gradually added to A with stirring, and the mixture was cooled with stirring to yield an O/W foundation.

It was confirmed that this O/W foundation gave a wrinkle improvement effect when applied to the skin.

TABLE 9

| O/W foundation | | |
|---|---|---|
| | | (% by mass) |
| A | Poly(ethylene glycol) | 0.5 |
| | 1,3-Butylene glycol | 2.0 |
| | Glycerol | 1.0 |
| | Pentylene glycol | 2.0 |
| | Ethanol | 1.0 |
| | Diglycerol | 0.5 |
| | Citric acid | 0.1 |
| | Sodium citrate | 0.1 |
| | Potassium hydroxide | 0.4 |
| | Triethanolamine | 0.4 |
| | Methylparaben | 0.2 |
| | Phenoxyethanol | 0.2 |
| | Pentasodium pentetate | 0.1 |
| | Phenylbenzimidazole sulfonic acid | 0.5 |
| | Ascorbic acid glucoside | 2.0 |
| | Xanthan gum | 0.1 |
| | Quince seed extract | 2.0 |
| | Golden silk extract | 0.5 |
| | Lotus extract | 0.5 |
| | Royal jelly fermented liquor | 0.5 |
| | Hydrochloride salt of Compound 1 | 1.0 |
| | Water | Balance |
| B | Mineral oil | 5.0 |
| | Petrolatum | 1.0 |
| | Microcrystalline wax | 1.0 |
| | Cetyl ethylhexanoate | 5.0 |
| | Glyceryl trioctanoate | 1.0 |
| | Hydrogenated rape oil | 1.0 |
| | Beeswax | 1.0 |
| | Dimethicone | 0.5 |
| | Methylphenyl polysiloxane | 0.5 |
| | Decamethylcyclopentasiloxane | 3.0 |
| | Crosslinked dimethicone | 0.5 |
| | t-Butyl methoxydibenzoylmethane | 1.0 |
| | Ethylhexyl methoxycinnamate | 1.0 |
| | Glyceryl oleate | 0.5 |
| | Polyglyceryl oleate | 0.5 |
| | Sorbitan isostearate | 1.0 |
| | PEG-20 stearate | 0.5 |
| | Sucrose stearate | 0.5 |
| | Polyoxyethylene phytostanol | 0.5 |
| | Polyoxyethylene polyglycerol stearyl ether | 0.5 |
| | Stearic acid | 1.5 |
| | Cetanol | 2.0 |
| | Behenyl alcohol | 1.0 |

TABLE 9-continued

O/W foundation

| | (% by mass) |
|---|---|
| (Alkyd acrylate/dimethicone) copolymer-treated and oxidized titanium | 9.0 |
| (Alkyd acrylate/dimethicone) copolymer-treated and oxidized Bengal red | 1.0 |
| (Alkyl acrylate/dimethicone) copolymer-treated and oxidized yellow iron oxide | 3.0 |
| (Alkyd aciylate/dimethicone) copolymer-treated and oxidized black iron oxide | 0.1 |
| Red No. 226 | 0.01 |
| Safflower red | 0.01 |
| Gardenia yellow | 0.01 |
| Gem Tone Ruby (produced by Engelhard Corp.) | 0.2 |
| Timiron Splendid Gold (produced by Merck & Co., Inc.) | 0.2 |
| Reflecks Pinpoints of Pearl (produced by Engelhard Corp.) | 0.2 |
| Trimethoxysilyl dimethicone-treated COLORONA GLITTER Bordeaux (produced by Merck & Co., Inc.) | 0.2 |
| Trimethoxysilyl dimethicone-treated GENESTAR 420 (produced by Nihon Koken Kogyo Co., Ltd.) | 0.2 |
| Trimethoxysilyl dimethicone-treated COVERLEAF MF (produced by JGC Catalysts and Chemicals Ltd.) | 0.2 |
| Perfluorooctyltriethoxysilane-treated COVERLEAF PC1035 (produced by JGC Catalysts and Chemicals Ltd.) | 0.2 |
| SILKYFLAKE FTD025FY-F02 (produced by Nippon Sheet Glass Co., Ltd.) | 0.2 |
| METASHINE MT1080KY (produced by Nippon Sheet Glass Co., Ltd.) | 0.2 |
| Talc | 3.0 |
| Fine particle titanium oxide ("MT-100SA", produced by Tayca Corporation) | 2.0 |
| Fine particle zinc oxide | 1.0 |
| Ethylhexylglycerin | 0.2 |
| Tocopherol | 0.1 |
| Perfume | 0.2 |
| Total | 100.0 |

Production Example 8

A W/O foundation which was an external preparation for skin of the present invention was prepared according to the recipe shown in Table 10. That is, the ingredients of A and B were heated at 80° C., and mixed together respectively, then A was gradually added to B with stirring, and the mixture was cooled with stirring to yield a W/O foundation.

It was confirmed that this W/O foundation gave a wrinkle improvement effect when applied to the skin.

TABLE 10

W/O foundation

| | (% by mass) |
|---|---|
| Poly(ethylene glycol) | 0.5 |
| 3-Butylene glycol | 5.0 |
| Glycerol | 1.0 |
| Pentylene glycol | 2.0 |
| Ethanol | 1.0 |
| Diglycerol | 0.5 |
| Citric acid | 0.1 |
| Sodium citrate | 0.1 |
| Potassium hydroxide | 0.4 |
| Methylparaben | 0.2 |
| Phenoxyethanol | 0.2 |
| Pentasodium pentetate | 0.1 |
| Phenylbenzimidazole sulfonic acid | 0.5 |
| Ascorbic acid glucoside | 2.0 |
| Xanthan gum | 0.1 |
| Hydrochloride salt of Compound 1 | 1.0 |
| Water | Balance |
| Mineral oil | 1.0 |
| Petrolatum | 0.5 |
| Microcrystalline wax | 0.5 |
| Cetyl ethylhexanoate | 1.0 |
| Glyceryl trioctanoate | 1.0 |
| Beeswax | 0.5 |
| Dimethicone | 0.5 |
| Methylphenylpolysiloxane | 1.0 |
| Decamethylcyclopentasiloxane | 14.0 |
| Crosslinked dimethicone | 0.5 |
| (Alkyl acrylate/dimethicone) copolymer | 0.5 |
| Trimethylsiloxysilicate | 0.5 |
| Caprylyl methicone | 0.5 |
| t-Butyl methoxybenzoylmethane | 1.0 |
| Ethylhexyl methoxycinnamate | 1.0 |
| Glyceryl oleate | 0.5 |
| Polyglyceryl oleate | 0.5 |
| Sorbitan isostearate | 0.5 |
| Sucrose stearate | 1.0 |
| Polyoxyethylene polyglycerol stearyl ether | 0.5 |
| PEG-10 Dimethicone | 3.0 |
| Dimethyl distearyl ammonium hectorite | 0.75 |
| (Alkyd acrylate/dimethicone) copolymer-treated and oxidized titanium | 8.0 |
| (Alkyd acrylate/dimethicone) copolymer-treated and oxidized Bengal red | 0.5 |
| (Alkyl acrylate/dimethicone) copolymer-treated and oxidized yellow iron oxide | 1.5 |
| (Alkyd acrylate/dimethicone) copolymer-treated and oxidized black iron oxide | 0.1 |
| Red No. 226 | 0.01 |
| Triethoxycaprylylsilane-treated Yellow No. 4 | 0.01 |
| Safflower red | 0.01 |
| Gardenia yellow | 0.01 |
| Gem Tone Ruby (produced by Engelhard Corp.) | 0.2 |
| Timiron Splendid Gold (produced by Merck & Co., Inc.) | 0.2 |
| Reflecks Pinpoints of Pearl (produced by Engelhard Corp.) | 0.2 |
| Trimethoxysilyl dimethicone-treated COLORONA GLITTER Bordeaux (produced by Merck & Co, Inc.) | 0.2 |
| Trimethoxysilyl dimethicone-treated GENESTAR 420 (produced by Nihon Koken Kogyo Co, Ltd.) | 0.2 |
| Trimethoxysilyl dimethicone-treated COVERLEAF MF (produced by JGC Catalysts and Chemicals Ltd.) | 0.2 |
| Perfluorooctyltriethoxysilane-treated COVERLEAF PC1035 (produced by JGC Catalysts and Chemicals Ltd.) | 0.2 |
| SILKYFLAKE FTD025FY-FOZ (produced by Nippon Sheet Glass Co, Ltd.) | 0.2 |
| METASHINE MT1080KY (produced by Nippon Sheet Glass Co, Ltd.) | 0.2 |
| Talc | 3.0 |
| Fine particle titanium oxide ("MT-100SA", produced by Tayca Corporation) | 1.0 |
| Fine particle zinc oxide | 0.5 |
| Ethylhexylglycerin | 0.2 |
| Tocopherol | 0.1 |
| Perfume | 0.2 |
| Total | 100.0 |

Production Example 9

An O/W sunscreen which was an external preparation for skin of the present invention was prepared according to the recipe shown in Table 11. That is, the ingredients of A and B were heated at 80° C., and mixed together respectively, then B was gradually added to A with stirring, and the mixture was cooled with stirring to yield an O/W sunscreen.

It was confirmed that this O/V sunscreen gave a wrinkle improvement effect when applied to the skin.

TABLE 11

| | O/W Sunscreen | (% by mass) |
|---|---|---|
| A | Poly(ethylene glycol) | 0.5 |
| | 1,3-Butylene glycol | 5.0 |
| | Glycerol | 1.0 |
| | Pentylene glycol | 1.0 |
| | Ethanol | 1.0 |
| | Diglycerol | 0.5 |
| | Citric acid | 0.1 |
| | Sodium citrate | 0.1 |
| | Potassium hydroxide | 0.4 |
| | Triethanolamine | 0.4 |
| | Methylparaben | 0.2 |
| | Phenoxyethanol | 0.2 |
| | Pentasodium pentetate | 0.05 |
| | Phenylbenzimidazole sulfonic acid | 0.2 |
| | Ascorbic acid glucoside | 2.0 |
| | Xanthan gum | 0.1 |
| | Hydrochloride salt of Compound 1 | 1.0 |
| | Water | Balance |
| B | Mineral oil | 1.0 |
| | Petrolatum | 0.5 |
| | Microcrystalline wax | 0.5 |
| | Cetyl ethylhexanoate | 1.0 |
| | Glyceryl trioctanoate | 4.0 |
| | Beeswax | 0.5 |
| | Dimethicone | 0.5 |
| | Methylphenylpolysiloxane | 0.5 |
| | Decamethylcyclopentasiloxane | 3.0 |
| | Crosslinked dimethicone | 0.5 |
| | (Alkyl acrylate/dimethicone) copolymer | 0.5 |
| | t-Butyl methoxydibenzoylmethane | 1.0 |
| | Ethylhexyl methoxycinnamate | 3.0 |
| | Glyceryl oleate | 0.5 |
| | Polyglyceryl oleate | 0.5 |
| | Sorbitan isostearate | 0.5 |
| | PEG-20 stearate | 0.5 |
| | Sucrose stearate | 0.5 |
| | Polyoxyethylene phytostanol | 0.5 |
| | Polyoxyethylene polyglycerol stearyl ether | 0.3 |
| | Na Cocomonoglyceride sulfate | 0.1 |
| | Na Stearoyl lactylate | 0.1 |
| | PEG-10 Dimethicone | 0.5 |
| | Stearic acid | 0.5 |
| | Cetanol | 1.0 |
| | Behenyl alcohol | 0.5 |
| | (Alkyl acrylate/dimethicone) copolymer-treated and oxidized titanium | 1.0 |
| | (Alkyl acrylate/dimethicone) copolymer-treated and oxidized Bengal red | 0.5 |
| | (Alkyl acrylate/dimethicone) copolymer-treated and oxidized yellow iron oxide | 0.1 |
| | (Alkyl acrylate/dimethicone) copolymer-treated and oxidized black iron oxide | 0.01 |
| | Red No. 226 | 0.01 |
| | Triethoxycaprylylsilane-treated Yellow No. 4 | 0.01 |
| | Safflower red | 0.01 |
| | Gardenia yellow | 0.01 |
| | Gem Tone Ruby (produced by Engelhard Corp.) | 0.1 |
| | Timiron Splendid Gold (produced by Merck & Co., Inc.) | 0.1 |
| | Reflecks Pinpoints of Pearl (produced by Engelhard Corp.) | 0.1 |
| | Trimethoxysilyl dimethicone-treated COLORONA GLITTER Bordeaux (produced by Merck & Co., Inc.) | 0.1 |
| | Trimethoxysilyl dimethicone-treated GENESTAR 420 (produced by Nihon Koken Kogyo Co., Ltd.) | 0.1 |

TABLE 11-continued

| | O/W Sunscreen | (% by mass) |
|---|---|---|
| | Trimethoxysilyl dimethicone-treated COVERLEAF MF (produced by JGC Catalysts and Chemicals Ltd.) | 0.1 |
| | Perfluorooctyltriethoxysilane-treated COVERLEAF PC1035 (produced by JGC Catalysts and Chemicals Ltd.) | 0.1 |
| | SILKYFLAKE FTD025FY-F02 (produced by Nippon Sheet Glass Co., Ltd.) | 0.1 |
| | METASHINE MT1080KY (produced by Nippon Sheet Glass Co., Ltd.) | 0.1 |
| | Talc | 1.0 |
| | Methyl methacrylate crosspolymer | 1.0 |
| | Fine particle titanium oxide ("M1100SA", produced by Tayca Corporation) | 6.0 |
| | Polyacrylate | 0.1 |
| | Fine particle zinc oxide | 2.0 |
| | Ethylhexylglycerin | 0.1 |
| | Tocopherol | 0.05 |
| | Perfume | 0.2 |
| Total | | 100.0 |

Production Example 10

A W/O sunscreen which was an external preparation for skin of the present invention was prepared according to the recipe shown in Table 12. That is, the ingredients of A and B were healed at 80° C., and mixed together respectively, then A was gradually added to B with stirring, and the mixture was cooled with stirring to yield a W/O sunscreen.

It was confirmed that this W/O sunscreen gave a wrinkle improvement effect when applied to the skin.

TABLE 12

| | W/O Sunscreen | (% by mass) |
|---|---|---|
| A | Poly(ethylene glycol) | 0.5 |
| | 1,3-Butylene glycol | 5.0 |
| | Glycerol | 1.0 |
| | Pentylene glycol | 2.0 |
| | Ethanol | 1.0 |
| | Diglycerol | 0.5 |
| | Citric acid | 0.1 |
| | Sodium citrate | 0.1 |
| | Potassium hydroxide | 0.4 |
| | Methylparaben | 0.2 |
| | Phenoxyethanol | 0.2 |
| | Pentasodium pentetate | 0.1 |
| | Phenylbenzimidazole sulfonic acid | 0.5 |
| | Ascorbic acid glucoside | 2.0 |
| | Xanthan gum | 0.1 |
| | Hydrochloride salt of Compound 1 | 1.0 |
| | Water | Balance |
| B | Mineral oil | 1.0 |
| | Petrolatum | 0.5 |
| | Microcrystallme wax | 0.5 |
| | Cetyl ethylhexanoate | 1.0 |
| | Glyceryl trioctanoate | 1.0 |
| | Beeswax | 0.5 |
| | Dimethicone | 0.5 |
| | Methylphenylpolysiloxane | 1.0 |
| | Decamethylcyclopentasiloxane | 14.0 |
| | Crosslinked dimethicone | 0.5 |
| | (Alkyl acrylate/dimethicone) copolymer | 0.5 |
| | Trimethylsiloxysilicate | 0.5 |
| | Caprylyl methicone | 0.5 |
| | t-Butyl methoxybenzoylmethane | 1.0 |
| | Ethylhexyl methoxycinnamate | 1.0 |

| W/O Sunscreen | |
|---|---|
| | (% by mass) |
| Glyceryl oleate | 0.5 |
| Polyglyceryl oleate | 0.5 |
| Sorbitan isostearate | 0.5 |
| Sucrose stearate | 1.0 |
| Polyoxyethylene polyglycerol stearyl ether | 0.5 |
| PEG-10 Dimethicone | 3.0 |
| Dimethyl distearyl ammonium hectorite | 0.75 |
| (Alkyl acrylate/dimethicone) copolymer-treated and oxidized titanium | 8.0 |
| (Alkyl acrylate/dimethicone) copolymer-treated and oxidized Bengal red | 0.5 |
| (Alkyl acrylate/dimethicone) copolymer-treated and oxidized yellow iron oxide | 1.5 |
| (Alkyl acrylate/dimethicone) copolymer-treated and oxidized black iron oxide | 0.1 |
| Red No. 226 | 0.01 |
| Triethoxycaprylylsilane-treated Yellow No. 4 | 0.01 |
| Safflower red | 0.01 |
| Gardenia yellow | 0.01 |
| Gem Tone Ruby (produced by Engelhard Corp.) | 0.2 |
| Timiron Splendid Gold (produced by Merck & Co., Inc.) | 0.2 |
| Reflecks Pinpoints of Pearl (produced by Engelhard Corp.) | 0.2 |
| Trimethoxysilyl dimethicone-treated COLORONA GLITTER Bordeaux (produced by Merck & Co., Inc.) | 0.2 |
| Trimethoxysilyl dimethicone-treatedGENESTAR 420 (produced by Nihon Koken Kogyo Co., Ltd.) | 0.2 |
| Trimethoxysilyl dimethicone-treated COVERLEAF MF (produced by JGC Catalysts and Chemicals Ltd.) | 0.2 |
| Perfluorohexylethyl trimethoxysilane-treated COVERLEAF PC1035 (produced by JGC Catalysts and Chemicals Ltd.) | 0.2 |
| SILKYFLAKE FTD025FY-F02 (produced by Nippon Sheet Glass Co., Ltd.) | 0.2 |
| METASHINE MT1080KY (produced by Nippon Sheet Glass Co., Ltd.) | 0.2 |
| Talc | 3.0 |
| Fine particle titanium oxide ("MT-100SA", produced by Tayca Corporation) | 1.0 |
| Fine particle zinc oxide | 0.5 |
| Ethylhexylglycerin | 0.2 |
| Tocopherol | 0.1 |
| Perfume | 0.2 |
| Total | 100.0 |

INDUSTRIAL APPLICABILITY

The wrinkle improving agent of the present invention exhibits an excellent wrinkle improvement effect, and therefore it is extremely useful industrially, such that it can be suitably contained in an external composition for skin for wrinkle improvement.

The invention claimed is:

1. A method for wrinkle improving comprising applying to skin having wrinkles an agent comprising a compound expressed by the following Formula, or an acid addition salt thereof to skin;

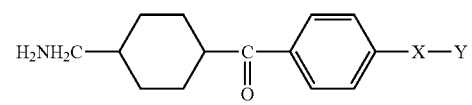

(1)

wherein X represents an alkylene group having 1 to 2 carbon atoms in which a hydrogen atom may be substituted with a methyl group, Y represents COOR$^1$ or CH$_2$OR$^2$, R$^1$ represents a hydrogen atom, or an optionally branched alkyl group having 1 to 6 carbon atoms, and R$^2$ represents a hydrogen atom, or an optionally branched acyl group having 1 to 6 carbon atoms.

2. The method according to claim 1, wherein the agent is contained in an external composition suitable for application to skin.

3. The method according to claim 2, wherein the external composition is a cosmetic formulation.

* * * * *